(12) United States Patent
Schwab et al.

(10) Patent No.: US 6,271,430 B2
(45) Date of Patent: *Aug. 7, 2001

(54) PREPARATION OF PROPENE

(75) Inventors: Peter Schwab, Bad Dürkheim; Arthur Höhn, Kirchheim, both of (DE)

(73) Assignee: BASF Aktiengesellschaft, Ludwigshafen (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/283,201

(22) Filed: Apr. 1, 1999

Related U.S. Application Data

(62) Division of application No. 08/935,661, filed on Sep. 23, 1997.

(30) Foreign Application Priority Data

Sep. 27, 1996 (DE) .............................. 196 40 026

(51) Int. Cl.$^7$ ...................................... C07C 6/02
(52) U.S. Cl. ................. 585/644; 585/313; 585/315; 585/324; 585/644; 585/646; 585/647
(58) Field of Search ................... 585/324, 313, 585/315, 644, 646, 647

(56) References Cited

U.S. PATENT DOCUMENTS 3,776,974 * 12/1973 Gautier et al. ................... 260/683 D

FOREIGN PATENT DOCUMENTS

1216278 * 12/1970 (GB).
691318 * 12/1970 (EP).

OTHER PUBLICATIONS

'Distillation Columns with Vertical Partitions'; Kabel; pp. 92–98, 1987.*

* cited by examiner

Primary Examiner—Marian C. Knode
Assistant Examiner—Thuan D. Dang
(74) Attorney, Agent, or Firm—Keil & Weinkauf

(57) ABSTRACT

The present invention relates to a process for preparing propene by metathesis of olefins. The process comprises preparing propene by a) in a first reactor (R1), reacting 1-butene and 2-butene to give propene and 2-pentene in the presence of a metathesis catalyst comprising at least one compound of a metal of transition group VIb, VIIb, or VIII of the Periodic Table of elements, b) subsequently separating the propene, unreacted raffinate II, and 2-pentene formed in a) in a distillation column (D1), c) subsequently reacting the 2-pentene of b) with ethene to give propene and 1-butene in a reactor (R2) in the presence of a metathesis catalyst comprising at least one compound of a metal of transition group VIb, VIIb, or VIII of the Periodic Table of Elements, d) subsequently separating the propene and 1-butene formed in c), e) subsequently returning the 1-butene formed in d) to step a) and f) wherein unreacted raffinate II is taken off at the middle off take of column D1 in b) and partly returned to step a).

2 Claims, 3 Drawing Sheets

PREPARATION OF PROPENE

This application is a divisional of Ser. No. 08/935,661 filed on Sep. 23, 1997.

The present invention relates to a process for preparing propene by metathesis of olefins.

BACKGROUND OF THE INVENTION

1. Field of the Invention

Olefin metathesis (disproportionation) in its simplest form describes the reversible, metal-catalyzed rearrangement of olefins by cleavage and reformation of C=C double bonds. For example, olefins of the formulae $R^1$—CH=CH—$R^2$ and $R^3$—CH=CH—$R^4$ are reversibly reacted to form olefins of the formulae $R^1$—CH=CH—$R^3$ and $R^2$—CH=CH—$R^4$. In the metathesis of acyclic olefins, a distinction is made between self-metathesis in which an olefin is converted into a mixture of two olefins having different molar masses and cross- or co-metathesis in which two different olefins react. An example of self-metathesis is the reaction of two molecules of propene to give ethene and 2-butene, as is performed, for example, by the Phillips triolefin process, see Hydrocarbon Processing, Volume 46, November 1967, No. 11, p. 232. An example of cross-metathesis is the reaction of propene and 1-butene to give ethene and 2-pentene. If one of the reactants is ethene, the reaction is customarily referred to as an ethenolysis.

The metathesis reactions are carried out in the presence of catalysts. Suitable catalysts for this purpose are, in principle, homogeneous and heterogeneous transition metal compounds, in particular those of transition groups VI to VIII of the Periodic Table of the Elements, as well as homogeneous and heterogeneous catalyst systems in which these compounds are present.

2. Description of the Prior Art

DE-A-19 40 433 discloses the metathesis of 1-butene with 2-butene to form propene and 2-pentene, with $Re_2O_7/Al_2O_3$ being used as catalyst. The 2-pentene formed is reacted further with sodium hydride on potassium carbonate and ethene to give heptenes.

The metathesis of 1-butene and 2-butene to give propene and 2-pentene is mentioned in K. L. Anderson, T. D. Brown, Hydrocarbon Processing, Volume 55, August 1978, No. 8, pp. 119–122 as a secondary reaction in the synthesis of isoamylene.

EP-A-0 304 515 discloses a metathesis process for reacting 1-butene with 2-butene to give propene and pentenes, which is carried out in a reactive distillation apparatus using $Re_2O_7/Al_2O_3$ as catalyst.

U.S. Pat. No. 3,526,676 discloses the metathesis of 1-butene with 2-butene to give propene and pentene. It is carried out over $MoO_3$ and $CoO$ on $Al_2O_3$.

U.S. Pat. No. 3,785,957 discloses a process for the production of fuel having a high octane number. In this process, an olefinic fuel is disproportionated together with ethylene, the product is fractionated into a propylene stream, a butene stream, a $C_5$- or $C_5$–$C_6$-olefin stream and a $C_{6+}$ or $C_{7+}$ fuel stream. The $C_5$- or $C_5$–$C_6$-olefin stream is disproportionated with ethene over a $WO_3/SiO_2$ fixed-bed catalyst to give propylene and butenes. The propylene obtained is disproportionated to form ethylene and butenes and the butenes are alkylated with isobutane.

U.S. Pat. No. 3,767,565 discloses a process for increasing the octane number of fuel in which a $C_5$ fraction of an olefinic fuel is reacted with ethylene in the presence of a catalyst comprising $WO_3/SiO_2$ and MgO to form ethylene, propylene, n-butenes and isobutenes. The propylene obtained is disproportionated and the resulting n-butenes are alkylated with isobutane.

EP-A1-0 691 318 discloses an olefin metathesis process in which $C_5$-olefins and ethylene are reacted in the presence of a catalyst to give mixed $C_4$-olefins and propene. Thus, 2-methyl-2-butene is reacted with ethene to give isobutene and propene. A mixture of 2-pentenes and 2-methyl-2-butene is reacted to give a mixture of 1-butene, isobutene and propene.

A process for preparing propene in high yield by reacting 1-butene and 2-butene is not known.

A process for preparing propene in high yield by from 2-butene without use of a large excess of ethene is not known.

BRIEF SUMMARY OF THE INVENTION

It is an object of the present invention to provide a process for preparing propene in high yield from 1-butene and 2-butene. A further object of the present invention is to provide a process for preparing propene from 2-butene in which an excess of ethene does not have to be employed. A further object of the present invention is to provide a process for recovering propene from $C_4$ streams which are low in 1-butene using as little ethene as possible. A further object of the present invention is to provide a process for preparing propene and 1-butene from 2-pentene.

We have found that these objects are achieved by a process for preparing propene and 1-butene by reacting 2-pentene with ethene in the presence of a metathesis catalyst comprising at least one compound of a metal of transition group VIb, VIIb or VIII of the Periodic Table of the Elements. The 2-pentene is here preferably obtained by reacting 1-butene and 2-butene in the presence of the above metathesis catalyst to give propene and 2-pentene and separating off the 2-pentene.

The process of the present invention comprises 2 metathesis steps. In the first step, 1-butene and 2-butene are reacted to give propene and 2-pentene. In a second step, 2-pentene is then reacted with ethene to give 1-butene and propene. According to one embodiment of the invention, the 1-butene is returned to the first reaction step.

The net reaction is thus the reaction of 2-butene with ethene to form 2 molecules of propene. According to one embodiment of the invention, the reaction of 2-pentene with ethene formally requires only equimolar amounts of starting materials in order to obtain the products in high yield. Thus, in contrast to the reverse triolefin process, the amount of ethene used can be kept small.

Both metathesis steps can be carried out as a reactive distillation, as is described below.

According to one embodiment of the invention, 1-butene and 2-butene can be used in the reaction as pure substances. According to another embodiment of the invention, the butenes are used in the form of a $C_4$ stream which originates, for example, from a cracker, in particular a steam cracker, or a refining process. This $C_4$ stream can comprise $C_4$-alkanes in addition to the butenes. According to an embodiment of the invention, use is made of a $C_4$ stream which consists of raffinate II. Raffinate II is here a fraction comprising 1-butene, cis/trans-2-butene, isobutene and also n-butane and iso-butane. For example, raffinate II can comprise 80–85% by weight of olefins and 15–20% by weight of butanes, with, for example, 25–50% by weight of 1-butene, 30–55% by weight of 2-butene and at most 1–2% by weight of isobutene. According to an embodiment of the invention, the $C_4$ stream used has a butene content of from 20 to 100% by weight, preferably from 50 to 90% by weight, in particular from 70 to 90% by weight. The ratio of 1-butene to 2-butene is from 10:1 to 1:10, preferably from 3:1 to 1:3, in particular 2:1 to 1:2. According to one embodiment of the invention, the $C_4$ stream can contain small amounts of other hydrocarbons.

According to an embodiment of the invention, the starting material used can be any stream in which 1-butene and 2-butene are present. According to one embodiment of the invention, the 1-butene can originate from the synthesis of the present invention itself and be mixed with introduced 2-butene.

The $C_4$ feedstream used is preferably pre-purified before use in the process of the present invention in order to remove any traces of water, oxygen or oxygenates, sulfur or sulfur-containing compounds, nitrogen phosphor or halogens, especially chlorides which may be present. The removal is preferably carried out by passing the $C_4$ feedstream over absorber material such as zeolites or zeolite-analoguous phosphates, oxides of silicon, aluminium, titanium, zirconium having a high surface area, bleaching earth, clays, hydrotalcites, phosphates having a high surface area, active carbon and carbon molecular sieves as well as organic polymers and ion exchange resins, preferably NaX molecular sieve. The absorber materials are preferably present as a guard bed.

Processes which can be used in the adsorption or adsorptive cleaning are for example described in W-Kast, Adsorption aus der Gasphase, VCH, Weinheim (1988). The use of zeolitic adsorbents is discussed in D. W. Breck, Zeolite Molecular Sieves, Wiley, New York (1974). The specific removal of acetaldehyde from $C_{3-15}$-hydrocarbons in liquid phase is described in EP-A-0 582 901.

The processes described in the above-mentioned literature can be applied in the present invention. Preferably the feedstream is contacted with adsorbents in the gaseous, liquid or supercritical phase.

Apart from the reaction of 1-butene and 2-butene to form propene and 2-pentene, a small proportion of 3-hexene and ethene can be obtained as by-product. In addition, small amounts of higher-boiling compounds can also be present.

The small amounts of by-products, which according to an embodiment of the invention make up from 1 to 20% by weight, preferably from 1 to 5% by weight, of the amount of 2-pentene formed, do not interfere in the subsequent reaction so that, according to one embodiment of the invention, no purification of the 2-pentene to remove these by-products is necessary before the further reaction. According to one embodiment of the invention, the 2-pentene is used in pure form in the secondary reaction.

Thus, the expression "2-pentene" also includes those mixtures comprising not only 2-pentene but also small amounts of hexenes, in particular 3-hexene, and other higher-boiling compounds.

Correspondingly, the expression "butenes", "1-butene" and "2-butene" also includes a mixture which comprises not only the butene or butenes but also $C_4$-alkanes, in particular butanes.

A number of embodiments of the invention are illustrated below with the aid of the drawing, in which

The abbreviations employed in the figures have the following meanings:

1-Bu: 1-butene
2-Bu: 2-butene
Bu: butanes
Et: ethene
Pr: propene
2-Pe: 2-pentene
3-He: 3-hexene
H: high boilers
II: raffinate II
C4: C4 olefins
$C5^+$: olefins having 5 or more carbon atoms
R1: reactor
R2: reactor
D1: distillation column (if a vertical line is shown under D1, the column is a dividing wall column)
D2: column (if a vertical line is shown under D2, the column is a dividing wall column)
D3: distillation column Described below is one embodiment of the process of the invention, comprising a) reaction of 1-butene and 2-butene to give propene and 2-pentene in the presence of a metathesis catalyst comprising at least one compound of a metal of transition group VIb, VIIb or VIII of the Periodic Table of the Elements, b) subsequent separation of the propene and 2-pentene formed, c) subsequent reaction of the 2-pentene with ethene to give propene and 1-butene in the presence of a metathesis catalyst comprising at least one compound of a metal of transition group VIb, VIIb or VIII of the Periodic Table of the Elements, d) subsequent separation of the propene and 1-butene formed, e) subsequent return of the 1-butene formed to step a).

Figure 1:
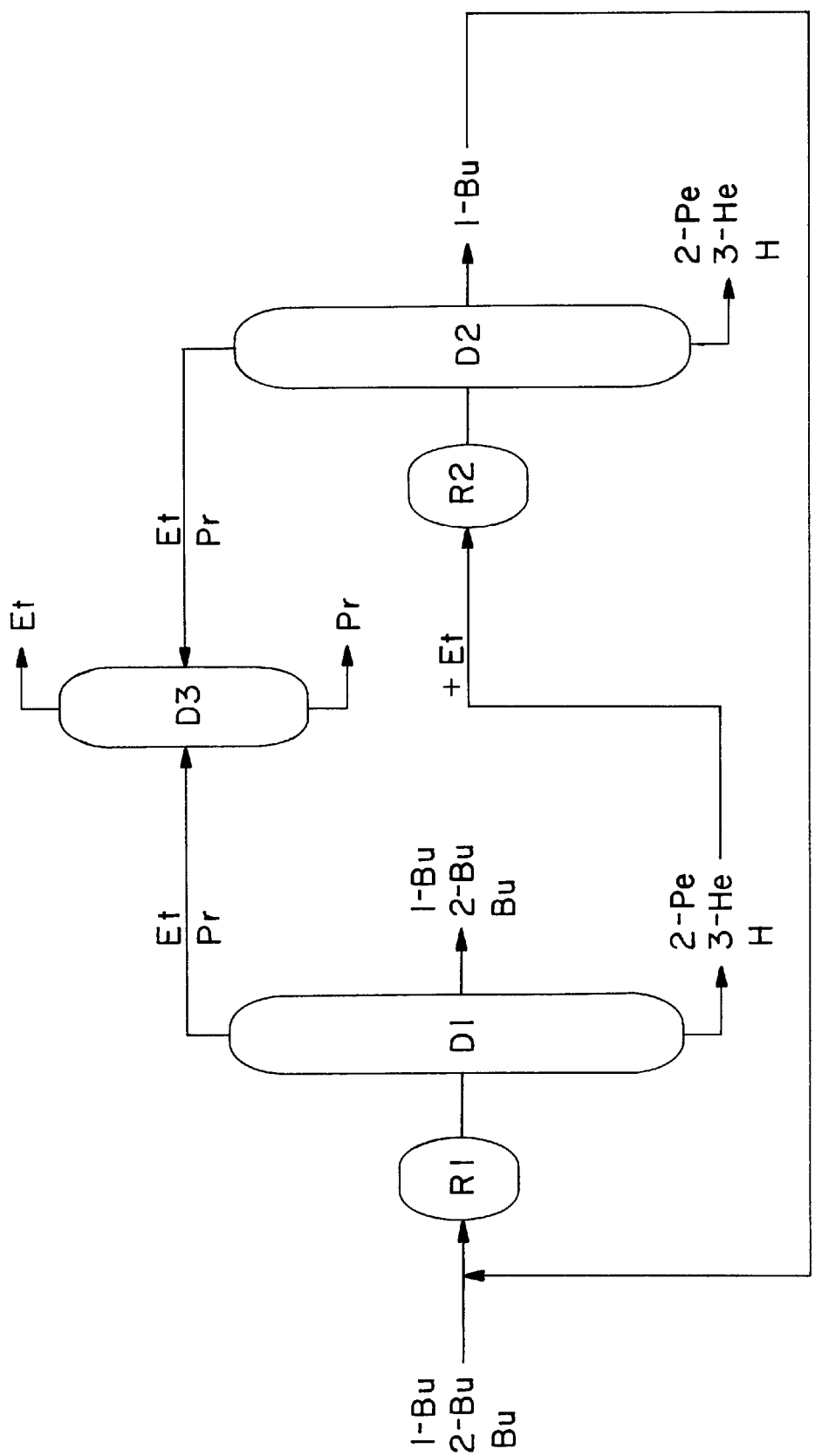
FIG. 1 schematically shows an embodiment of the process of the invention

This embodiment is shown in FIG. 1.

In a first reactor R1, 1-butene and 2-butene are reacted in the presence of the metathesis catalyst of the present invention to give propene and 2-pentene. For this purpose, a raffinate II stream is fed to the reactor. The reactor is followed by a distillation column D1 at the top of which propene and ethene formed as by-product are removed. Unreacted raffinate II is taken off at the middle offtake. Some of it may also be returned to the reactor R1 (not shown in FIG. 1). 2-Pentene and 3-hexene formed as by-product as well as high boilers are taken off at the bottom of D1. The bottoms are then fed together with added ethene to a reactor R2 which again contains a metathesis catalyst of the present invention. In this reactor R2, the reaction of 2-pentene with ethene to give 1-butene and propene takes place. The reaction product from reactor R2 is fed to a distillation column D2 at the top of which propene and unreacted ethene are taken off. 1-Butene formed is taken off at the middle offtake and at least some of it is preferably returned to the reactor R1. Unreacted 2-pentene and also, as by-products, 3-hexene and high boilers are obtained at the bottom of D2. These are preferably returned to the reactor R2. The mixtures of propene and by-product ethene taken off at the top of D1 and D2 are fractionated in a further distillation column D3. Ethene is obtained at the top of D3 and this is preferably returned to the reactor R2 (not shown in FIG. 1), or discharged as co-cracker feed. The propene obtained at the bottom of D3 is the desired reaction product of the process of the present invention. D1 and D2 are designed such that a low-boiling phase, in particular a $C_{2/3}$ phase comprising ethene and propene, is taken off at the top of the column. $C_4$ streams, in particular butenes and butanes, are taken off as intermediate-boiling phase. As bottoms, $C_{\geq 5}$-hydrocarbons are discharged.

The reactors R1 and R2 can be any suitable reactors. They can serve for continuous or batchwise operation. Thus, according to one embodiment, they can be pressure vessels such as glass pressure vessels, while according to a further embodiment they can be tube reactors.

According to an embodiment of the invention, the total conversion in R1 is from 20 to 90%, preferably from 50 to 80%.

According to an embodiment of the invention, the total conversion in R2 is from 20 to 100%, preferably from 60 to 90%.

The reaction in R1 preferably takes place in the liquid phase. Here, pressure and temperature are selected such that the reactants remain in the liquid phase.

According to an embodiment of the invention, the temperature in R1 is from 0 to 150° C., preferably from 20 to 80° C. According to an embodiment of the invention, the pressure is from 2 to 200 bar, preferably from 5 to 20 bar. The reaction in R2 (ethenolysis) is, according to an embodiment of the invention, carried out at from 0 to 150° C., preferably from 20 to 80° C., under an ethene pressure of from 5 to 200 bar, preferably from 30 to 80 bar. Further ethene can be injected continuously so that a constant pressure is maintained.

The reactions in R1 and R2 can be carried out for a time of from one second to ten hours, preferably from 1 to 60 minutes.

The distillation columns D1 and D2 are, according to an embodiment of the invention, columns which allow separation of a hydrocarbon stream into $C_{2/3}$ streams, $C_4$ streams and $C_{\geq 5}$ streams. The columns can be designed as dividing wall columns. According to an embodiment of the invention, D3 is a column which allows the separation of ethene and propene. According to one embodiment of the invention, the reactor R1 is combined with the distillation column D1 to form a reactive distillation apparatus. Here, the reaction is carried out directly in the distillation column. The catalyst is present in the reaction column so that the distillation is carried out simultaneously with the reaction or immediately thereafter. A corresponding process is known under the name "reactive distillation".

According to one embodiment, reactor R2 and distillation column D2 are combined to form a reactive distillation apparatus in which the reaction and distillation are combined as in the above-described reactive distillation.

According to one embodiment of the invention, both reactions take place in reactive distillation apparatuses. Both reactions are equilibrium reactions so that, according to one embodiment of the invention, the process products are removed as quickly as possible from the equilibrium to achieve as high as possible a conversion. This is possible, in particular, when using reactive distillation apparatuses.

Figure 2:
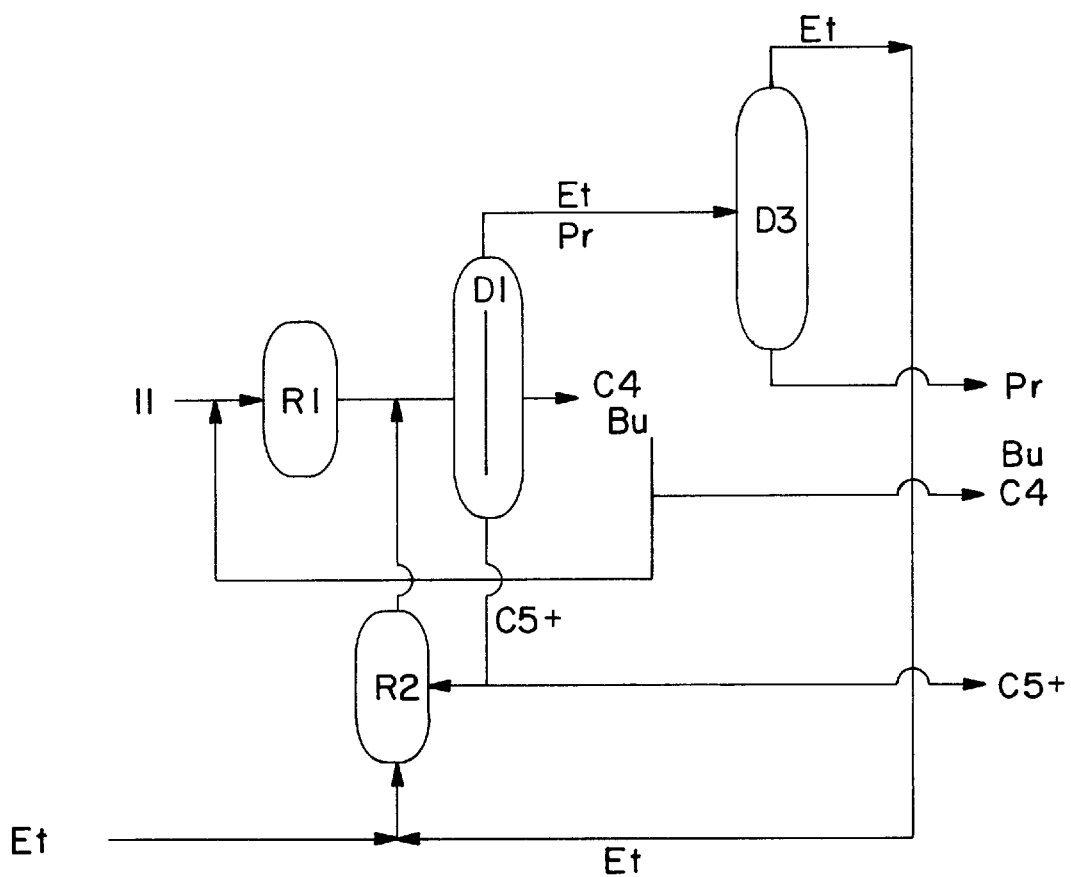
FIG. 2 shows a further embodiment of the process of the invention.

In place of a normal distillation column D1, a dividing wall column can be provided. Such a process is shown in FIG. 2. The process shown is additionally modified compared with that shown in FIG. 1.

As in the above-described embodiment, a metathesis is carried out over a heterogeneous metathesis catalyst in the reactor R1, using raffinate II. The distillation column D1 serves to separate the reaction products formed in the metathesis. The distillation column D3 serves to separate ethene and propene. The reactor R2 is for the reaction of $C_5^+$ high boilers with ethene.

Unlike the previous embodiment, the distillation column D1 is configured as a dividing wall column. In addition, some of the intermediate-boiling product from D1, which comprises $C_4$ olefins and butanes, is returned to the raffinate II feedstream. Since the distillation columns D1 and D2 have to perform the same separation task, only one such distillation column D1 is provided in this embodiment. This allows the outlay in terms of apparatus to be reduced. The reaction scheme was adapted correspondingly: the high-boiling product from D1 is fed to the reactor R2 or some of it is discharged. The output from the reactor R2 is fed to the distillation column D1. Part of the ethene feed to the reactor R2 is from the low-boiling product from the distillation column D3 and the other part is additional ethene fed in. The output from the process consists of propene as main product and in addition $C_4$ olefins and $C_5^+$ olefins.

Figure 3:
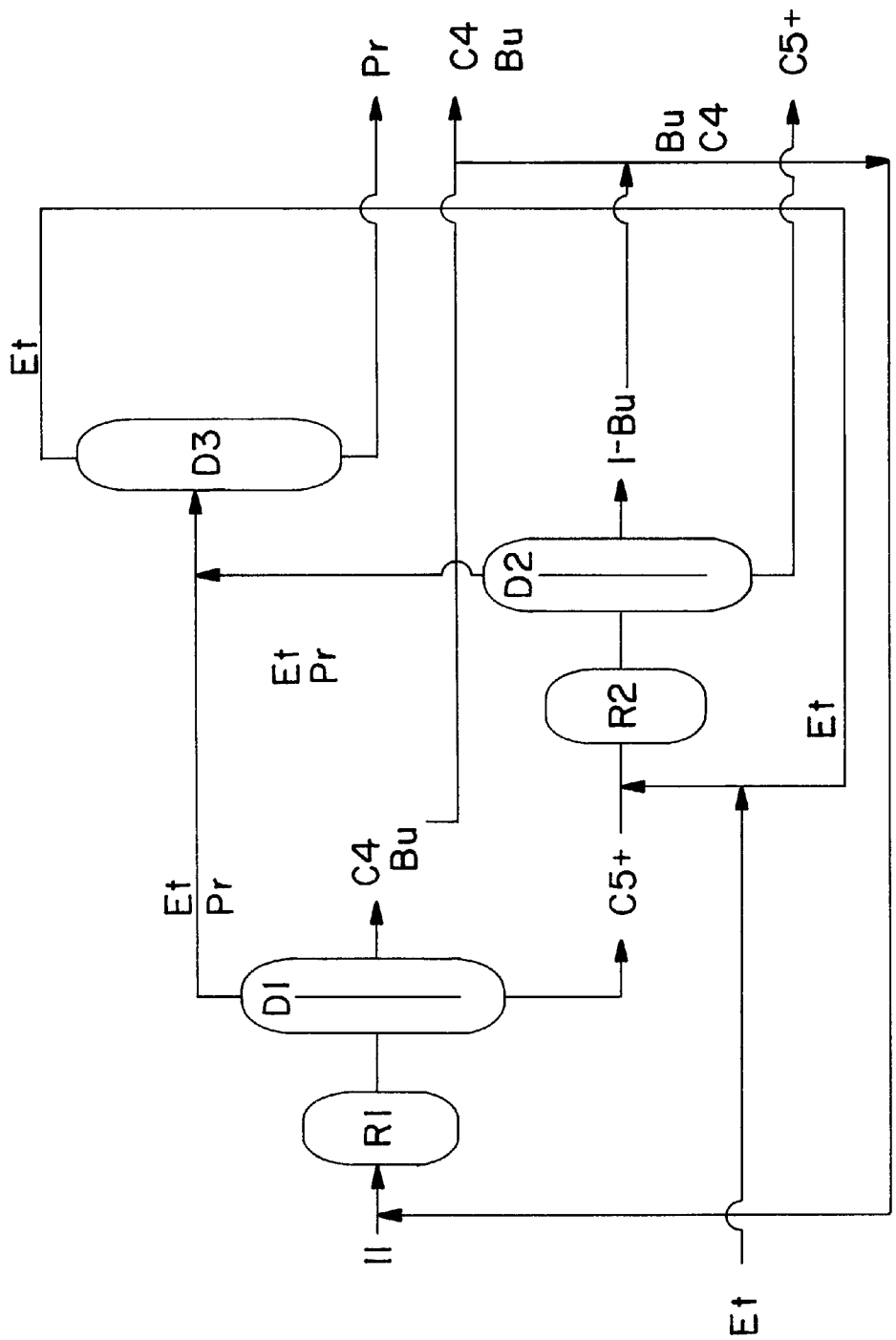
FIG. 3 shows a further embodiment of the process of the invention.

FIG. 3 shows an embodiment of the process of the present invention which largely corresponds to the embodiment shown in FIG. 1. The column D2 is, like the column D1, configured as a dividing wall column.

Unlike the process shown in FIG. 1, some of the intermediate-boiling product from D1, which comprises $C_4$ olefins and butanes, is discharged and some of it is combined with the intermediate-boiling product from the column D2 and returned to the reactor R1. The ethene obtained from the distillation column D3 is fed to the reactor R2 in which the reaction with the $C_5^+$ fraction takes place. Again, propene as main product and parts of the $C_4$ olefin fraction and butanes and also the $C_5^+$ fraction from the distillation column D2 (also as co-cracker feed) are discharged.

Catalyst

All suitable metathesis catalysts can be used in the process of the present invention.

According to an embodiment of the invention, the catalyst is a heterogeneous catalyst, in particular a supported catalyst. According to an embodiment of the invention, the catalyst comprises at least one compound of a metal of transition group VIb, VIIb or VIII of the Periodic Table of the Elements. The catalyst preferably comprises a ruthenium compound and/or rhenium compound.

According to an embodiment of the invention, the metal compound is a metal oxide, partial oxide with additional organic radicals or a carbonyl compound.

According to one embodiment of the invention, a homogeneous catalyst is used. The catalyst is here at least one compound of a metal of transition group VIb, VIIb or VIII of the Periodic Table of the Elements. Preference is given to using rhenium or ruthenium in the metal compounds.

According to one embodiment of the invention, use is made of ruthenium compounds as are described in WO 93/20111 and WO 96/04289.

According to a preferred embodiment of the invention, use is made of $RuX_2(CHR)(PR'_3)_2$, where the radicals R and R' are $C_1$–$C_{12}$-alkyl radicals, preferably $C_1$–$C_6$-alkyl radicals, or $C_6$–$C_{12}$-aryl radicals, $R^1$ is particularly preferably a $C_3$–$C_8$-cycloalkyl radical, in particular a $C_5$- or $C_6$-cycloalkyl radical, and X is a halide such as chloride, bromide or iodide.

In particular, $RuCl_2(=CHPh)(PCy_3)_2$ is used according to the present invention, according to one embodiment of the invention as solution, for example in methylene chloride.

The metal compound is preferably an oxide of rhenium, in particular $Re_2O_7$.

Support

According to an embodiment of the invention, the catalysts of the present invention comprise a support. Supports employed here are, in particular, inorganic supports such as $Al_2O_3$, in particular $\gamma$-$Al_2O_3$, $SiO_2$, $Fe_2O_3$, or mixtures thereof such as $SiO_2/Al_2O_3$, $B_2O_3/SiO_2/Al_2O_3$ or $Fe_2O_3/Al_2O_3$.

The metal oxide content on the support is, according to one embodiment of the invention, from 1 to 20% by weight, preferably from 3 to 15% by weight, in particular from 8 to 12% by weight, based on the total weight of the supported catalyst.

The catalyst used is preferably $Re_2O_7$ on $Al_2O_3$, $SiO_2/Al_2O_3$, $SiO_2/Al_2O_3/Fe_2O_3$ or $B_2O_3/Al_2O_3$. The proportion of metal oxide here is preferably from 1 to 20% by weight, particularly preferably from 3 to 10% by weight. According to one embodiment of the invention, $MeReO_3$ is used in place of $Re_2O_7$ or in admixture therewith.

According to the present invention, particular preference is given to using $Re_2O_7$ on $Al_2O_3$.

According to one embodiment of the invention, the catalysts are used in freshly calcined form and then require no further activation, for example by means of alkylating agents. Deactivated catalysts can, according to the present invention, be regenerated by burning off carbon residues, for example at 550° C. in a stream of air and cooling under argon.

The reactions of the present invention can be carried out in the presence of a solvent, for example a hydrocarbon solvent. According to a preferred embodiment of the invention, the reactions are carried out without further added solvent.

The invention also provides apparatuses for carrying out the process described. One apparatus for carrying out the process as shown in FIG. 2 comprises a metathesis reactor (R1) for reacting 1-butene with 2-butene whose outlet leads to a distillation column (D1), which can be configured as a dividing wall column, for separating $C_{2/3}$ low-boiling, $C_4$ intermediate-boiling and $C_5^+$ high-boiling phases, where the low boiler outlet leads to a column (D3) for separating ethene and propene, the intermediate boiler outlet leads to the reactor (R1) or to discharge and the high boiler outlet leads to a reactor (R2) for reacting 2-pentene with ethene whose outlet leads to the column (D1) or to discharge, where the ethene outlet from the column (D3) and an ethene feed line lead to the reactor (R2).

An apparatus for carrying out the process as shown in FIG. 3 comprises a metathesis reactor (R1) for reacting 1-butene with 2-butene whose outlet leads to a distillation column (D1), which can be configured as a dividing wall column, for separating $C_{2/3}$ low-boiling, $C_4$ intermediate-boiling and $C_5^+$ high-boiling phases, where the low boiler outlet leads to a column (D3) for separating ethene and propene, the intermediate boiler outlet leads to the reactor (R1) or to discharge and the high boiler outlet leads to a reactor (R2) for reacting 2-pentene with ethene whose outlet leads to a distillation column (D2), which can be configured as a dividing wall column, for separating $C_{2/3}$ low-boiling, $C_4$ intermediate-boiling and $C_5^+$ high-boiling phases, where the low boiler outlet leads to the column (D3), the intermediate boiler outlet together with the intermediate boiler outlet from (D1) leads to the reactor (R1) and the high boiler outlet leads to discharge, where the ethene outlet from the column (D3) and an ethene feed line lead to the reactor (R2).

The invention is illustrated by the examples below.

DESCRIPTION OF THE PREFERRED EMBODIMENTS

EXAMPLE 1 to 6

Batchwise Synthesis of Propene from Raffinate II

In a pressure vessel having a capacity of 100 ml, 50 ml of raffinate II (having a ratio of 1-butene to 2-butene of 1:2) were stirred with 10 g of a freshly calcined heterogeneous catalyst at 60° C. and 7 bar. The catalysts used are shown in the following table. Samples were taken at intervals of 5 minutes and analyzed by gas chromatography. The 1-butene conversions and propene selectivities based on the composition of the mixtures after 15 minutes are shown below.

TABLE

| EXAMPLE | CATALYST | CONVERSION OF 1-BUTENE | SELECTIVITY TO PROPENE |
|---|---|---|---|
| 1 | 3% $Re_2O_7/Al_2O_3$ | 63% | 93% |
| 2 | 10% $Re_2O_7/Al_2O_3$ | 85% | 92% |
| 3 | 3% $Re_2O_7/SiO_2/Al_2O_3$ | 70% | 91% |
| 4 | 3% $Re_2O_7/SiO_2/Al_2O_3/Fe_2O_3$ | 38% | 88% |
| 5 | 3% $Re_2O_7/B_2O_3/Al_2O_3$ | 68% | 92% |
| 6 | 3% $MeReO_3/Al_2O_3$ | 41% | 89% |

Propene selectivities based on 1-butene of at least 88% are obtained for all catalysts. In particular, the catalyst comprising 3% of $Re_2O_7$ on $Al_2O_3$ displayed a selectivity of 93%. The conversion of 1-butene was in the range from 38 to 85%.

EXAMPLE 7

Homogeneously Catalyzed Synthesis of Propene from Raffinate II

In a pressure vessel having a capacity of 100 ml, 50 ml of raffinate II (having a 1-butene:2-butene ratio of 1:2) were admixed at room temperature with a solution of 31 mg (0.04 mmol) of $RuCl_2(=CHPh)(PCy_3)_2$ in 5 ml of methylene chloride. Samples were taken at intervals of 2 minutes and analyzed by gas chromatography. The 1-butene conversion after 10 minutes was 81%, the propene selectivity was 90%.

EXAMPLE 8

The reaction mixtures obtained as described in Examples 1 to 7 were fractionated by distillation, with 2-pentene and 3-hexene as by-product being obtained as high-boiling bottom product. In a pressure vessel having a capacity of 100 ml, 50 ml of this high-boiling bottom product was treated with 50 bar of ethene in the presence of 10 g of the 10% $Re_2O_7/Al_2O_3$ catalyst from Example 2. The pressure was maintained by continuous injection of further ethene at 60° C. Samples were taken at intervals of 2 minutes and analyzed by gas chromatography. After 20 minutes, the following composition of the mixture had been established:

Conversion (2-pentene and 3-hexene)=64%

Selectivity (1-butene and propene)=96%.

The above results show that the process of the present invention is very suitable for preparing propene from raffinate II streams (2-butene and 1-butene).

EXAMPLE 9

Continuous Synthesis of Propene from Raffinate II

Raffinate II is passed continuously at 60° C. and a pressure of 10 bar at different residence times through a flow tube containing an $Re_2O_7/Al_2O_3$ heterogeneous catalyst.

The catalyst from Example 1 was used. The reaction product was, after depressurization, analyzed by gas chromatography. The results are shown in the following table.

| Residence time [min] | Conversion of 1-butene | Conversion of total n-butenes | Selectivity to propene |
|---|---|---|---|
| 20 min | 75% | 59% | 80% |
| 10 min | 78% | 56% | 83% |
| 5 min | 79% | 55% | 85% |

The space-time yields achieved are in the range of 200–2000 g of propene/l·h.

EXAMPLE 10

The processes according to Examples 1 to 9 were repeated, the feedstream employed contained, however, approximately 40 to 50 ppm water and 60 to 80 ppm oxygenates. According to one process variant the feedstream was reacted directly, according to another process variant the gaseous feedstream was led over molecular sieve 13× (NaX-zeolite), whereby water and oxygenates were removed. The stability time of the metathesis catalyst was prolonged by a factor of 10 to 20 when the feed was led over the molecular sieve 13× first.

What is claimed is:

1. A process for preparing propene by
   a) passing a raffinate II stream comprising a mixture of 1-butene and 2-butene obtained from a refinery process over absorber materials to purify the raffinate II stream by removing water, oxygen, sulfur, nitrogen, phosphorus or halogens, passing the purified raffinate II stream into a first reactor (R1),
   b) reacting the 1-butene and 2-butene in raffinate II in the presence of a metathesis catalyst comprising at least one compound of a metal of transition group VIb, VIIb or VIII of the Periodic Table of elements to give propene and 2-pentene,
   c) subsequently passing the effluent from reactor R1 to a distillation column (D1) wherein the effluent is separated into low boiling $C_{2-3}$ hydrocarbons, intermediate boiling $C_4$ hydrocarbons and high boiling $C_{5+}$ hydrocarbons,
   d) passing at least a portion of the high boiling $C_{5+}$ hydrocarbons together with added ethene to reactor R2 for reaction in the presence of a metathesis catalyst comprising at least one compound of a metal of transition group VIb, VIIb or VIII of the Periodic Table of elements to give a mixture containing 1-butene and propene,
   e) subsequently passing the effluent from reactor R2 to distillation column (D1),
   f) subsequently passing the stream of low boiling $C_{2-3}$ hydrocarbons from distillation column (D1) to a distillation column (D3) for separation into ethene and propene and passing the ethene to metathesis reactor R2,
   g) passing at least a portion of the intermediate boiling $C_4$ hydrocarbons to reactor R1 and optionally removing any remaining intermediate boiling $C_4$ hydrocarbons from the system,
   h) continuously passing the effluents from Reactors R1 and R2 to distillation column D1 subsequently returning the 1-butene formed in d) to step a) and, recovering the propene.

2. A process as claimed in claim 1, wherein step c) is carried out in a dividing wall column.

* * * * *